(12) United States Patent
Stevens

(10) Patent No.: US 9,574,974 B2
(45) Date of Patent: Feb. 21, 2017

(54) SUSPENDED SEDIMENT SAMPLER

(71) Applicant: Thomas Charles Stevens, Townsville (AU)

(72) Inventor: Thomas Charles Stevens, Townsville (AU)

( * ) Notice: Subject to any disclaimer, the term of this patent is extended or adjusted under 35 U.S.C. 154(b) by 240 days.

(21) Appl. No.: 14/303,013

(22) Filed: Jun. 12, 2014

(65) Prior Publication Data
US 2014/0366655 A1  Dec. 18, 2014

(30) Foreign Application Priority Data
Jun. 13, 2013  (AU) .................................. 2013206318

(51) Int. Cl.
*G01N 1/12* (2006.01)
*G01N 1/10* (2006.01)
*G01N 1/20* (2006.01)

(52) U.S. Cl.
CPC .......... *G01N 1/10* (2013.01); *G01N 2001/1025* (2013.01); *G01N 2001/2071* (2013.01)

(58) Field of Classification Search
USPC ............................................. 73/964, 964.63
See application file for complete search history.

(56) References Cited

U.S. PATENT DOCUMENTS

| | | | | | |
|---|---|---|---|---|---|
| 3,481,712 | A | * | 12/1969 | Bernstein | B01L 3/5021 215/227 |
| 3,697,227 | A | * | 10/1972 | Goldstein et al. | B01L 3/502 422/409 |
| 4,271,704 | A | * | 6/1981 | Peters | G01N 1/12 116/264 |
| 4,326,427 | A | * | 4/1982 | Ueberschaer | G01N 1/12 73/864.65 |
| 4,762,009 | A | * | 8/1988 | Scrudto | G01N 1/2035 73/863.21 |
| 5,256,314 | A | * | 10/1993 | Driessen | G01N 33/491 210/361 |
| 5,507,194 | A | * | 4/1996 | Scavuzzo | G01N 1/12 73/864.63 |
| 5,902,940 | A | | 5/1999 | Stern | |
| 6,276,220 | B1 | * | 8/2001 | Varhol | G01N 1/12 73/863.21 |
| 6,457,486 | B1 | | 10/2002 | Pratt | |
| 6,457,760 | B1 | | 10/2002 | Pratt | |

(Continued)

FOREIGN PATENT DOCUMENTS

GB  566752 B1  1/1945

*Primary Examiner* — Clayton E Laballe
*Assistant Examiner* — Warren K Fenwick
(74) *Attorney, Agent, or Firm* — Tredecim LLC; Sean L. Sweeney

(57) ABSTRACT

The invention relates to a sampler for sampling sediment suspended in fluid, the sampler including a container and a closure. The container includes an opening through which fluid can enter and be contained therein. The closure is associated with the opening of the container and includes a moveable part which on tipping or inversion of the sampler moves between an open and a closed position. In the opened position, the sample can enter the container through the opening and be contained therein, and in the closed position, fluid in the container is substantially prevented from leaving the container. The invention also relates to variant forms of the invention and a method of use.

20 Claims, 6 Drawing Sheets

(56) References Cited

U.S. PATENT DOCUMENTS

| | | | | |
|---|---|---|---|---|
| 7,255,380 B1* | 8/2007 | Pratt | ................ | G01N 1/12 |
| | | | | 294/68.25 |
| 2013/0305845 A1* | 11/2013 | Rod | ................ | G01N 1/12 |
| | | | | 73/864.63 |

* cited by examiner

SUSPENDED SEDIMENT SAMPLER

CROSS-REFERENCE TO RELATED APPLICATIONS

This application incorporates by reference and claims priority to Australian Patent Application No. 2013206318 filed Jun. 13, 2013

BACKGROUND TO THE INVENTION

The present invention relates to a suspended sediment sampler and in particular to a suspended sediment sampler that can be tipped or inverted without losing the sample.

Sediment traps are well-known as an invaluable tool for collecting particulates found in water. Trapped particulates provide information on sediment levels, runoff changes and contaminants in a particular body of water or fluid that can be used for environmental and other studies and reports.

Known traps are generally large, expensive and cumbersome pieces of equipment adapted for deep sea sampling. There is a significant cost to deploying and retrieving these large traps, requiring lifting equipment and well trained personnel in careful use and calibration of the equipment. These traps are difficult to bring aboard and during the retrieval process the trap may be disturbed or tipped losing all or some of the sample contained therein. Some smaller rudimentary sediment traps are known but these are extremely vulnerable to loss of the sampled material due to tipping or inversion. The tipping or inversion may occur in rough weather or most commonly during retrieval.

Coastal waters, as compared to deep sea waters, have different challenges with tidal depth and access limitations, wave surge, poor fluid visibility, increased human interference, all increasing the risk of tipping and the loss of the sample. It is desirable to sample coastal waters and for there to be an easy, safe and efficient method of doing so.

The inventor sought to find a product, research or other information on alternative samplers to the deep sea sediment traps of which he was aware. He was unsuccessful in finding any suitable sampler, that was economic, robust and simple to produce and deploy, and that resists loss of the sampled material. In response to this identified need the inventor carefully researched means of producing a suspended sediment sampler that could be easily deployed and retrieved. Further, the inventor sought to develop a means of preserving the sample, even if the sampler was inverted during deployment or retrieval.

Through careful experimentation the inventor has developed a sediment sampler that is a significant improvement on known traps and will have numerous uses, for many different industries.

Throughout the specification and claims the invention is described with reference to sampling of suspended sediment in fluid. The invention can equally be used to sample other particulate matter and it is not intended that the invention be limited to use for sampling suspended sediment. For example, the invention may be used to sample any suitable particulate matter in a liquid, air, or other gas.

For clarity, any prior art referred to herein, does not constitute an admission that the prior art forms part of the common general knowledge, in Australia or elsewhere.

It is an object of the present invention to provide an improved sediment sampler that at least ameliorates one or more of the aforementioned problems of the prior art.

SUMMARY OF THE INVENTION

Accordingly, the present invention provides a sampler for sampling sediment suspended in fluid, the sampler including:
  a container including an opening through which fluid can enter and be contained therein; and
  a closure associated with the opening of the container the closure including a moveable part which on tipping or inversion of the sampler moves between an open and a closed position,
wherein in the open position the sample can enter the container through the opening and be contained therein, and in the closed position fluid in the container is substantially prevented from leaving the container.

Alternatively, the invention also provides a sampler for sampling sediment suspended in fluid, the sampler including:
  a container including an opening through which fluid can enter; and
  a closure associated with the opening of the container which on tipping or inverting of the sampler, substantially closes the opening to reduce loss of the sample from the container.

The sediment to be sampled may be any form of sediment. The sediment may be naturally occurring, man-made or a combination thereof. The sediment sampler may be used to sample any particulate matter in fluid, not limited to sediment. The sediment may be any particulate or suspended matter that it is desired to sample.

Preferably, the sediment sampler is adapted to collect any sediment or other suspended particulate matter in the fluid. Preferably, the sediment sampler is adapted for sediment testing sea water. Preferably, the sediment sampler is adapted for use in any aquatic environment including rivers, estuaries or dams. The sediment sampler may be adapted for sampling in chemical settlement ponds. The fluid may be any fluid it may be desirable to sample for particulate or suspended content. The fluid may be water. The fluid may be a gas. The fluid may be air. Where the fluid is air, the air may contain suspended particulates it is desired to sample.

Preferably, the sediment sampler is substantially made of a plastics material. Preferably, one or more components of the sediment sampler is made of a rigid plastics material. The sediment sampler and any of the components may be made of a suitable plastic, metal or other material or combination of materials. The sediment sampler and any of the components may include a coating. The coating may be an anti-fouling coating. The coating may be a chemically reactive resistant coating.

Preferably, the fluid is water containing suspended particulates. The fluid may be seawater, freshwater or estuary water. The fluid may be any liquid. The fluid may be any fluid it may be desired to sample, for example in industry, mining plants or chemical settlement ponds. The fluid may be a gas. The fluid may be air which it is desired to test. The fluid may be air containing suspended particulate materials.

Preferably, the sample is the fluid and or suspended particulates captured within the container that it is desired to study and or test.

Preferably, a housing is included. Preferably, the housing is adapted to correspond to the configuration of the container. In one form of the invention the container is a bottle with a circular cross-section and the housing cylindrical and sized to comfortably receive the bottle inside. The housing may take any suitable configuration or form. The housing may be circular, square, triangular or irregular in cross-section. The housing may be in the form of a tube shape. Preferably, the housing is made of a lightweight material. Preferably, the housing is made from a material that floats in water. Preferably, the housing is made from plastic. Preferably, the other components of the sampler all fit within and are protected by the housing. Preferably, the housing includes an opening at the top through which fluid can enter. Preferably, the sedimentary sample enters through the top of the housing and enters the container for capture.

Preferably, the container is held within the housing. The container may be supported within the housing. Preferably, the container is held and supported within the housing. Preferably, the container is removably held within the container. Preferably, a support for the container is included. The support may take any suitable form to support the container within the housing. The support may be a planar piece that fits within the housing and is adapted to receive a neck of the container therethrough. A neck support may be included. The neck support may be associated with the housing. The neck support may be associated with the container. Preferably, a neck support is included to support around the opening of the container. The neck support may support a neck of the container. The neck support may support the closure mechanism. The neck support may be made of plastic, metal or other suitable materials. The neck support may be a circular neck similar to that of a conventional bottle. Preferably, the neck support surrounds the opening of the container and supports it within a housing.

Preferably, the container is in the form of a bottle. The container may take any suitable form to contain the sample. The container may be circular, rectangular including square, triangular or irregular in cross-section, for example. The bottle is preferably a plastic bottle. Alternatively the container may be made of any suitable material including plastic, metal or other suitable materials or combination of materials. Preferably, the container is adapted for receipt of a sedimentary sample. The container may be interchangeable so that different containers can be used. For example, a smaller or large container may be used for different deployments. The sampler may, in one form of the invention, include more than one container.

Preferably, a funnel is included to direct fluid that enters the sampler into the container. Preferably, a funnel is included and the funnel is held within the housing of the sampler to direct fluid that enters the sampler to enter the container. Preferably, the funnel is made of a suitable rigid plastics material. Preferably, the opening of the funnel is proximal to the opening of the sampler, which may be an opening of a housing. The opening of the funnel may be sized to be of similar dimensions to the opening of the sampler. Alternatively, the opening of the funnel may be sized differently, or positioned below the level of the opening of the sampler. Most preferably, the funnel includes an outlet and the outlet is in fluid communication with the opening of the container to substantially capture fluid that enters the sampler.

Preferably, the opening of the container is sized to be suitable for receipt of fluid for sampling. Preferably, when a housing is included fluid enters the housing before entering the container through the opening. The opening may take any suitable size or form. Preferably, the opening is a round opening. The opening may be circular, rectangular including square, triangular, irregular or any other suitable shape. The width of the opening may be adapted for different deployments, for example, a larger mouth or opening may be used where there is a high incidence of sediment to enable an accurate sample to be taken.

Preferably, the opening of the container is in fluid communication with an outlet of a funnel and is adapted to direct the flow of fluid from the opening in the sampler or housing into the container with minimal loss of sample. The junction between the funnel and the opening of the container may be adapted for receipt of the closure means. The junction between the outlet of the funnel and the opening of the container may form part of the closure means.

The closure may take any suitable form. Preferably, the closure at least partially closes the opening on tipping of the sampler. Preferably, the closure substantially closes the opening on inversion of the sampler. Preferably, tipping of the sampler causes the closure to substantially prevent loss of the sample from the container by blocking the opening. Preferably, tipping of the sampler causes the closure means to substantially prevent loss of the sample from the container. Preferably, inversion of the sampler causes the closure to substantially prevent loss of the sample from the container by blocking the opening. Preferably, inversion of the sampler causes the closure to completely block the opening preventing the sample contained within from escaping. Most preferably, as the sampler tips the closure starts to close and on full inversion the closure completely blocks the opening preventing loss of the contained sample. The closure may block the opening, or stopper the container or in any other suitable way prevent fluid in the container from escaping.

Preferably, the closure includes a moveable part which on tipping or inversion of the sampler moves between an open and a closed position wherein in the open position fluid can enter the container through the opening and in the closed position the sample in the container is to at least some extent prevented from leaving the container. Preferably, the closure moves between the open and closed position during tipping and inversion of the sampler. There may be stages of opening or closing of the opening. Preferably, in the closed position the sample is substantially maintained within the container. Preferably, the closure in the closed position blocks the opening to substantially prevent fluid from leaving the container.

Preferably, the closure includes a recess corresponding to a moveable part of the closure, the recess being in communication with the opening, and the moveable part moves into the recess during tipping or inversion to substantially close the opening. The recess may be an extension of the opening of the container. The recess may be an extension of the outlet of a funnel. The recess may be an extension of the opening of the container and or of the outlet of a funnel which directs fluid into the container. The recess may be formed between and or from an extension of the outlet of a funnel and the opening of the container to form a recess.

Preferably, in one form of the invention, the closure includes a moveable part with a rounded end. Preferably, the closure includes a moveable part with a rounded end and a corresponding recess and during tipping or inversion of the sampler the rounded end of the moveable part falls under gravity into the recess to substantially block the opening and prevent the sample escaping. Preferably, the closure is a shuttle valve including a shuttle and corresponding recess. One or more part of the shuttle valve and or recess may include a friction resistant coating. One or more part of the shuttle valve and or recess may include a chemically inert coating. Preferably, the shuttle valve and recess include a friction resistant and chemically inert coating. Preferably, the friction resistant and chemically inert coating is TEFLON (trade mark).

The closure may lie within the opening and move between an open position, where fluid can enter the container, and a closed position, where the fluid sample is substantially prevented from leaving the container.

Preferably, in another form of the invention, the moveable part includes a rod moveable between an open position and a closed position, under gravity, to substantially block the opening. Preferably, in the open position the rod lies in the opening but does not block it allowing fluid to enter the container around the rod. Preferably, in the closed position the opening is substantially blocked to prevent the sample leaving the container.

Preferably, the rod includes a seal and the seal closes and substantially seals the opening of the container when the sampler is tipped or inverted. Preferably, the rod is a shuttle rod with a shuttle part at one end and a rod at the other and the rod is positioned in the opening such that tipping or inversion of the shuttle rod causes an end of the rod to block the opening. Preferably, the rod includes an O-ring or similar seal at the end configured to seal the opening when the sampler is inverted.

Preferably, in a further alternative form of the invention the closure includes one or more weight. The weight may be made of any suitable heavy material, for example lead, steel or other metal or other suitable material. Preferably, a pair of weights is included. The weight may be hung on wires, strings or the like. The weight may take any suitable shape. Preferably, the weight hangs down under gravity when the sampler is in an upright position, and this is the open position. Preferably, in the open position fluid can pass into the container. Preferably, on tipping or inversion of the sampler the weight prevents the sample leaving the container, to at least some extent, and this is the closed position. Preferably, on inversion the weight causes the opening of the container to be substantially closed or blocked.

Preferably, the closure includes a tube. Preferably, the tube extends into the opening of the container. The tube may fill the opening of the container. Preferably, the tube lies within the opening of the container and fluid entering the sampler can enter the container through the tube in an open position and the sample is substantially prevented from leaving the container in a closed position.

Preferably, the tube deforms or crumples when the sampler is tipped to substantially block the opening and prevent the sample leaving the container. Preferably, the tube deforms or crumples when the sampler is tipped or inverted as the tube is no longer pulled down by gravity by the weight and as the tube deforms or crumples the opening to the container is closed, at least to some extent.

Preferably, the tube is formed of a non-rigid material. Preferably, the tube is made from a thin-walled material. Preferably, the tube is made of a material prone to deformation or crumpling. Preferably, the tube must be maintained in a position to allow fluid into the container and in any other position the tube deforms and substantially prevents the sample leaving the container. Preferably, the tube crumples on tipping or inversion of the sampler and substantially prevents the sample leaving the container. Preferably, a funnel is included and the tube extends below the outlet of the funnel. Preferably, a neck support is included and the tube is suspended from the neck support. The neck support may narrow the opening of the container.

Alternatively, the tube may be suspended from any suitable point to hang within the opening of the container. A funnel may be included and the outlet of the funnel is surrounded by a neck support and the tube hangs below a junction of the outlet of the funnel and the neck support to hang within the opening of the container.

Preferably, one or more weight is included, suspended below the tube. There may be a pair of weights attached on opposite sides of the tube. Preferably, the weight hangs under gravity in the upright position so that the tube allows fluid into the container. Preferably, in the event the sampler tips the weight is pulled under gravity closing the tube to at least some extent. Preferably, when the sampler is inverted the weight causes the tube to block the opening of the container and substantially prevent the sample from escaping. Preferably, the tube crumples when the sampler is tipped as the tube is no longer pulled down by gravity by the weights. Preferably, as the tube crumples the opening to the container is closed at least to some extent.

The closure means may be associated with the opening in any suitable manner. Preferably, the closure means surrounds the opening. In other forms of the invention the closure lies within the opening. The closure may include a recess or other shaped part in communication with the opening. The closure may be inside, around or otherwise associated with the opening.

The tipping of the sampler may be due to weather, tide, outside influences, or any other cause. The tipping of the sampler may be to any extent. For example, the tipping may be slight tipping, or more significant tipping away from the upright position. The tipping may be a complete or partial inversion of the sampler. The tipping may be caused by retrieval of the sampler.

One or more baffles may be included. The baffles may lie across an opening in the housing of the sampler. The baffles may lie across the opening to the container. The baffles may be one or more strips. Preferably, several baffles are included to substantially prevent debris entering the sampler. Preferably, one or more baffles are included to substantially prevent debris entering the sampler and or to reduce turbulence and increase efficiency. The nature of the baffles may be varied to suit the particular application to be made of the sampler. The baffles may be made of a suitable plastic or other suitable material.

The sampler may be deployed on a frame. The frame may be used to support and assist to orientate the sampler in the fluid. The frame may take any suitable form. The frame may be in the form of a cage around the sampler. The frame may be a metal cage. The frame may be made of any suitable materials including plastic. The frame may be removably attached to a line, mobile surface float, object or structure in or near the fluid to be sampled. The frame may be attached to a mobile surface float. The sampler may be deployed in a body of water and the frame attached to a line, object or structure in the body of water.

Preferably, the sampler can include devices or instruments. For example, the sampler may include a device chosen from the following group: optical devices; electrochemical devices; electrical devices; mass sensitive devices; magnetic devices; biological devices; flow instruments; pressure instruments; temperature instruments; conductivity instruments; acoustic instruments; chemical measurement instruments; electromagnetic spectrum instruments such as image capturing instruments; communication instruments; mobility instruments; and or global positioning system ("GPS").

Preferably, one or more part includes a chemically inert coating. Preferably, one or more part includes an anti-fouling coating. Preferably, one or more part of the sampler includes a TEFLON (trade mark) coating.

Accordingly, the present invention provides, in a variant, a sampler for sampling suspended sediment, the sampler including:
- a container including an opening through which fluid can enter; and
- a closure, including a recess and a shuttle valve, associated with the opening of the container, and on tipping or inverting of the sampler the shuttle valve falls under gravity into the recess to substantially close the opening to reduce loss of the sample.

Accordingly, the present invention provides in a further variant a sampler for sampling suspended sediment, the sampler including:
- a container including an opening through which fluid can enter; and
- a shuttle rod lying within the opening of the container which on tipping or inverting of the sampler substantially closes the opening to reduce loss of the sample from the container.

Accordingly, the present invention provides in a further variant a sampler for sampling suspended sediment, the sampler including:
- a container including an opening through which fluid can enter; and
- a closure including a non-rigid tube and one or more weights which cause the tube to hang down under gravity allowing fluid to enter the container, and on tipping or inverting of the sampler, the weights cause the tube to deform or crumple closing the opening of the container and substantially reducing loss of the sample from the container.

Accordingly, the invention also provides a method of use of a sampler for sampling suspended sediment suspended in fluid, the sampler including a container having an opening and a closure associated with the opening including a moveable part which on tipping or inversion of the sampler moves between an open and a closed position, the method including the steps of:
a) deploying the sampler in fluid;
b) capturing fluid and associated suspended particulates in the sampler over time;
c) retrieving the sampler;
and the closure substantially maintains the sample in the container during tipping or inversion.

Preferably, the tipping or inversion is during retrieval.

The sediment sampler of the method may be the sediment sampler of the invention as defined above, in any of its forms or variants.

BRIEF DESCRIPTION OF THE DRAWINGS

The invention will now be described in connection with non-limiting preferred embodiments with reference to the accompanying drawings, in which.

DETAILED DESCRIPTION

Figure 1:
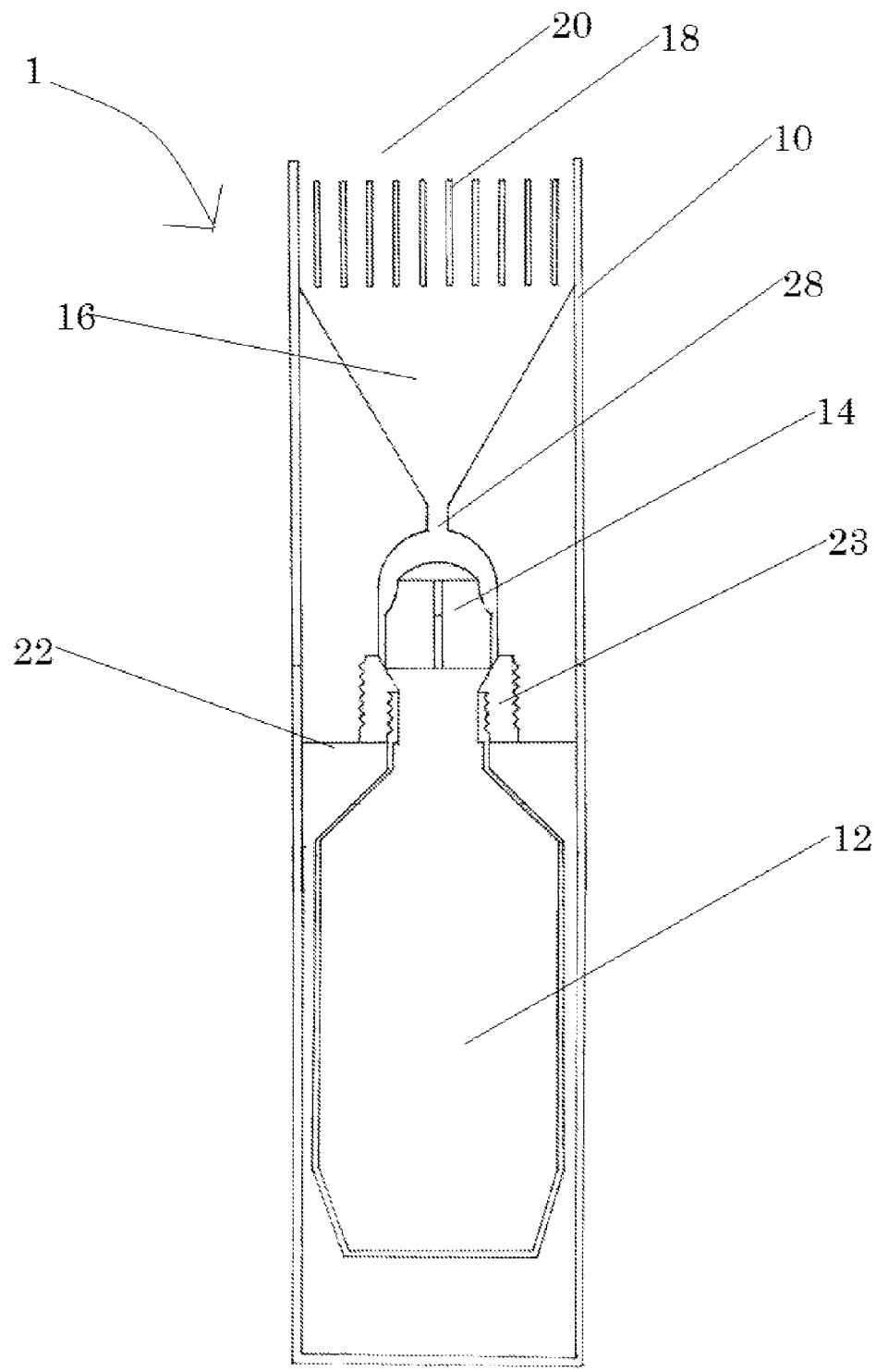
FIG. 1 is a schematic cross-sectional view of a suspended sediment sampler according to a first preferred embodiment of the invention.
Figure 2:
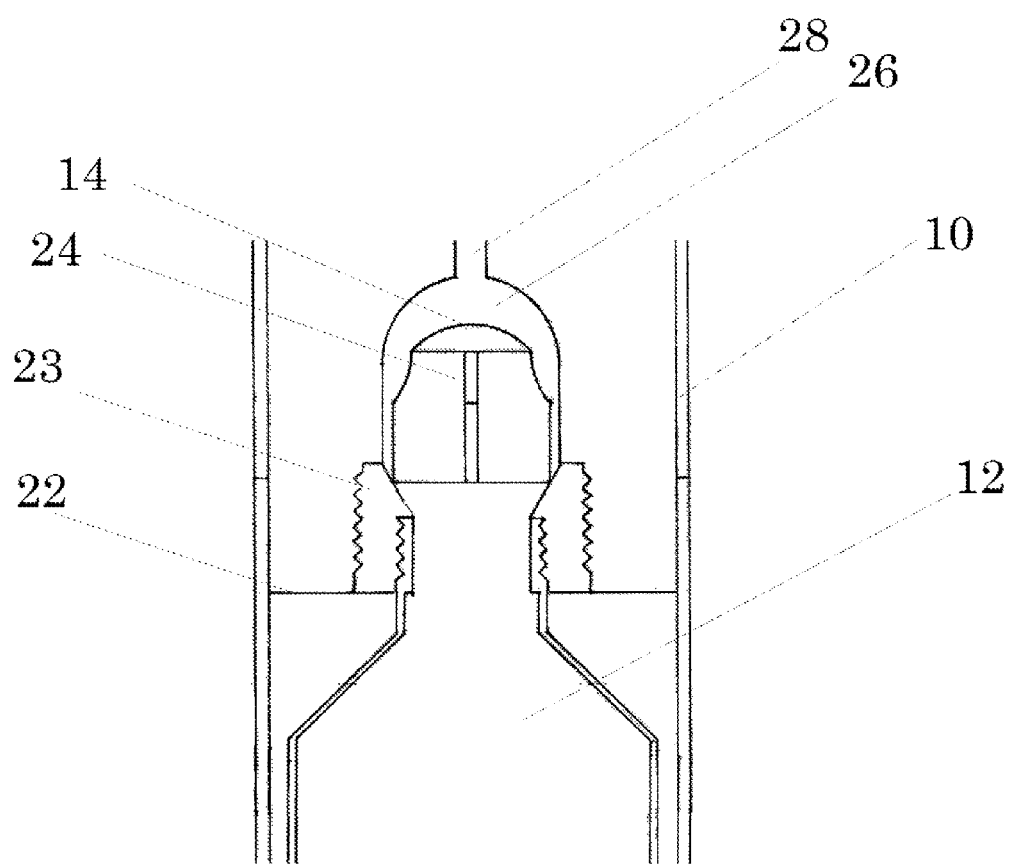
FIG. 2 is a detailed schematic cross-sectional view of the closure mechanism of the sediment sampler of FIG. 1.

Referring to FIGS. 1 and 2, a first preferred embodiment of the invention will be described, where sampler 1 includes housing 10 within which lies container 12, closure mechanism 14, funnel 16 and baffles 18. Each of the three preferred embodiments have these same components differing only in the form of closure mechanism 14, as described further below. Sampler 1 and components are generally made from a rigid plastic material, but alternative materials including aluminium or stainless steel could also be used.

Fluid enters through top opening 20 of housing 10, and is directed by funnel 16 to closure mechanism 14 and into container 12. It is the fluid containing the suspended particulates that form the sample to be collected. Container 12 is shown as a circular based plastic bottle of a known form, as is convenient for ease of sourcing and replacement. The particular shape, form and material of container 12 can be varied to suit the particular application. For example, container 12 could be made of aluminium and formed integrally with housing 10, in a variant to the invention.

Top opening 20 as illustrated is circular, as housing 10 is cylindrical in shape, and circular in cross section. Clearly other shapes of housing 10 and top opening 20 can be used such as square, oval or irregular in cross-section. Housing 10 and funnel 16 are illustrated as made of a strong plastic material as is an economic and light material. Alternatively, steel or metal or other materials could be used or a combination of materials used for housing 10 and funnel 16.

Baffles 18 prevent large materials entering sampler 1, for example leaves, feathers or rubbish that may be in the fluid. Baffles 18 works well to protect the integrity of the sample to fluid with suspended particulates. Baffles 18 also reduce turbulence of the flow, increasing efficiency. As shown baffles 18 are a series of plastic baffles across opening 20. Other materials may be used instead for baffles 18. Baffles 18 are very useful but could be omitted in one form of the invention.

Container 12 is held in place in housing 10 by support 22 attached within housing 10. Neck 23 is attached to support 22 and holds a neck (not labelled) of container 12 in place. The components of sampler 1 can be assembled during manufacture or can be assembled by the user before deployment.

Closure mechanism 14 of the first preferred embodiment includes valve shuttle 24 and corresponding recess 26 attached to opening 28 of funnel 16. On tipping or inversion of sampler 1, valve shuttle 24 falls under gravity into recess 26 and blocks opening 28 of funnel 16, preventing fluid from leaving container 12. Shuttle valve 24 and corresponding recess 26 as illustrated are made of stainless steel with a TEFLON (Trade mark) covering to facilitate the smooth and frictionless movement from an upright to an inverted position. Shuttle valve 24 and corresponding recess 26 could be made from other suitable materials including plastic, or combination of materials. Use of materials that prevent fouling or are chemically inert is preferable.

In use, sampler 1 is deployed in coastal waters, for example, by attachment to a suitable buoy. A metal frame may be used within which sampler 1 is supported in a box like structure. The box like structure may alternatively be a plate or mounting suitable to support sampler 1. Use of the frame is optional. Usually numerous samplers 1 will be deployed over a wide area in a body of water to test the particulate content and sediment over an area. Samplers 1 are allowed to stay in the fluid for a period of time which may be several days after which samplers 1 are retrieved. Retrieval is by means of hooking with a suitable grabbing device or similar and pulling sampler 1 up and into the boat or ship. It is quite usual for there to be significant tipping or inversion of the sampler during the retrieval, which may be compounded by high seas or bad weather generally. Use of sampler 1 minimises loss of the sample as if sampler 1 is tipped toward inversion, shuttle valve 24 falls under gravity into recess 26 to block opening 28 of funnel 16. In this way the sample in container 12 is prevented from escaping until a person wishes to remove the sample. To remove the sample sampler 1 is disassembled so that container 12 and the sample within can be accessed directly. Use of shuttle valve 24 is particularly beneficial as it does not rely on complex parts or electronics so it is anticipated that the item will be able to continue to be reused for many years, without need for replacement of shuttle valve 24.

Figure 3:
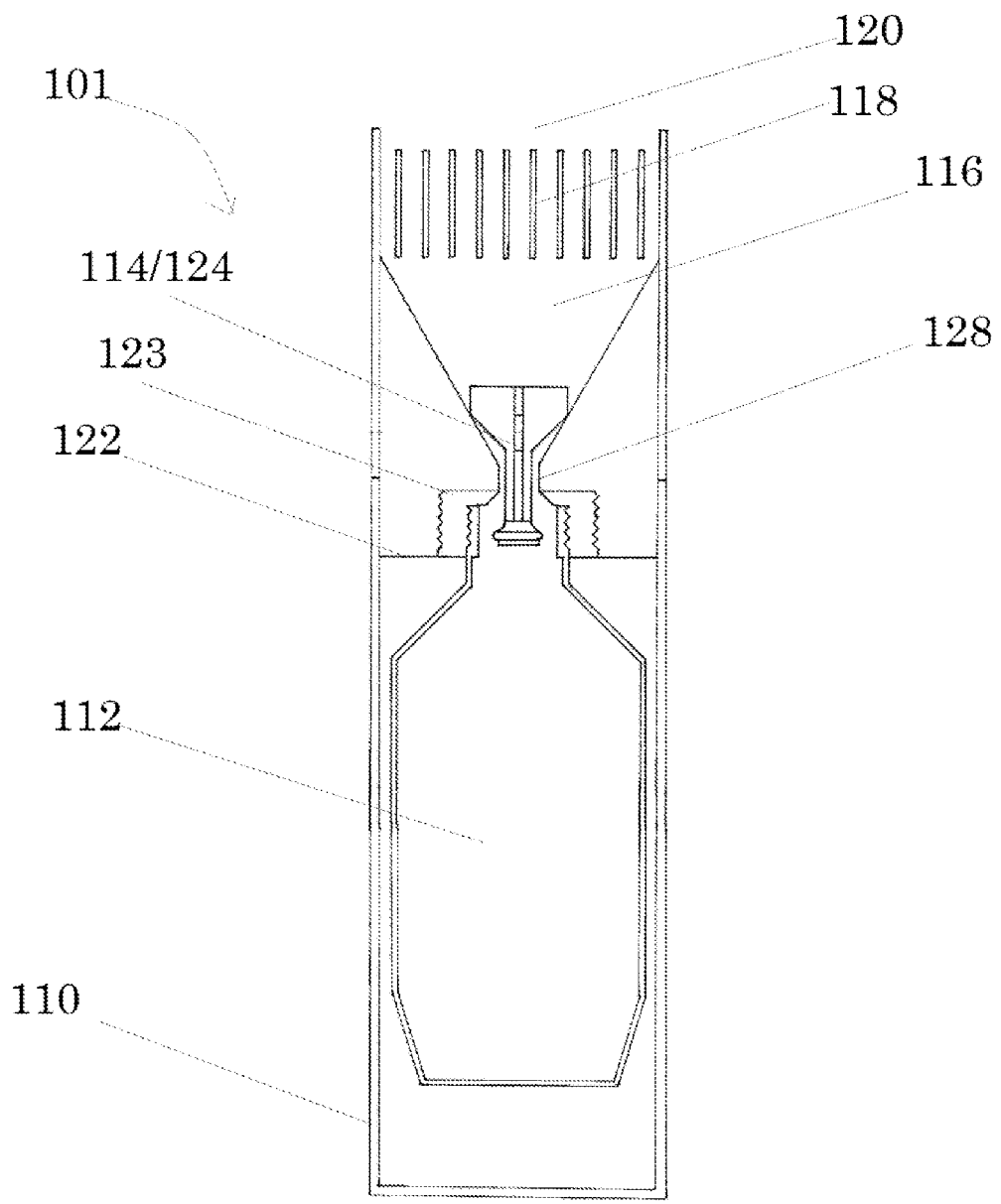
FIG. 3 is a schematic cross-sectional view of a suspended sediment sampler according to a second preferred embodiment of the invention.
Figure 4:
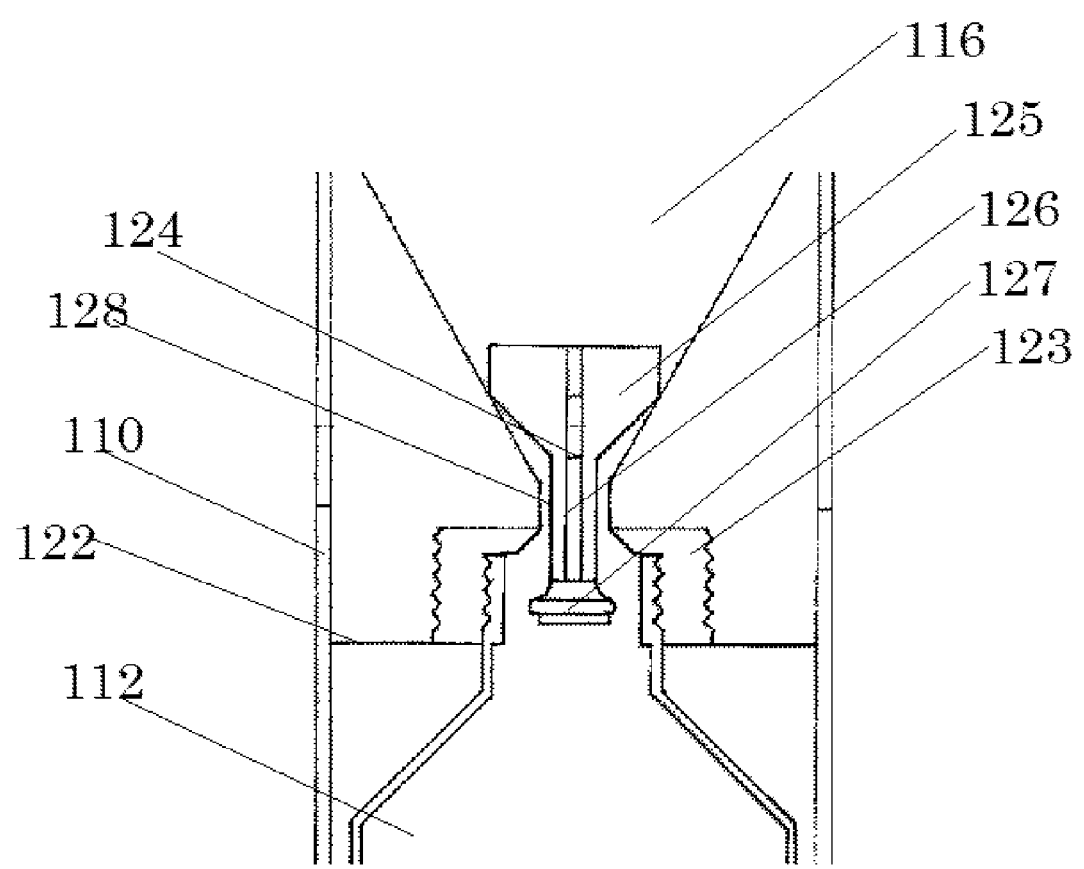
FIG. 4 is a detailed schematic cross-sectional view of the closure mechanism of the sediment sampler of FIG. 3.

Referring to FIGS. 3 and 4, a second preferred embodiment of the invention will be described, similar to the first and with similar reference numerals used for ease of reference. Sampler 101 includes housing 110 within which lies container 112, closure mechanism 114, funnel 116 and baffles 118. Sampler 101 is shown made of a rigid plastics material, but alternative suitable materials may be used.

Fluid enters through top opening 120 of housing 110, directed by funnel 116 to closure mechanism 114 and into container 112. Container 112 is shown again as a plastic bottle, but other containers may be used instead.

Top opening 120 as illustrated is circular, as housing 110 is cylindrical in shape, circular in cross section and made of plastic, as is funnel 116. Again metal or other materials or combination of metals could be used for housing 110 and funnel 116.

Baffles 118 prevent large materials entering sampler 101 and reduces turbulence improving efficiency. Baffles 118 are made of strips of a plastics material but again metal or other materials could be used instead.

Container 112 is held in place in housing 110 by support 122 attached within housing 110. Neck 123 is attached to support 122 and holds a neck (not labelled) of container 112 in place. The components of sampler 101 can be assembled during manufacture or assembled by the user prior to use.

Closure mechanism 114 of the second preferred embodiment works in a similar fashion to the first embodiment but is slightly different. Shuttle rod 124 has shuttle part 125 and rod 126, with O-ring 127 attached to the end of rod 128. Shuttle rod 124 lies in funnel 116 with shuttle part 125 in the point of funnel 116, rod 126 passing through funnel opening 128 and into the top opening of container 112. Rod 126 is configured to readily move up and down within funnel opening 128 under gravity if sampler 110 is inverted and then returned to upright. When inverted rod 126 falls under gravity towards funnel 116 O-ring 127 on the end of rod 126 fills and seals funnel opening 116 preventing the sample in container 112 from being lost. Use of O-ring 127 assists to quickly seal funnel opening 116 so that less or no fluid or sample is lost if inverted.

In use, sampler 101 is deployed in fluid to be tested. Again a metal frame may be used within which sampler 101 is supported. Use of sampler 101 minimises loss of the sample as if sampler 101 is tipped toward inversion shuttle rod 124 falls under gravity so rod 126 falls such that O-ring 127 seals the sample within container 112, preventing loss of the sample. The sealing of O-ring 127 is particularly advantageous in this form of the invention.

Figure 5:
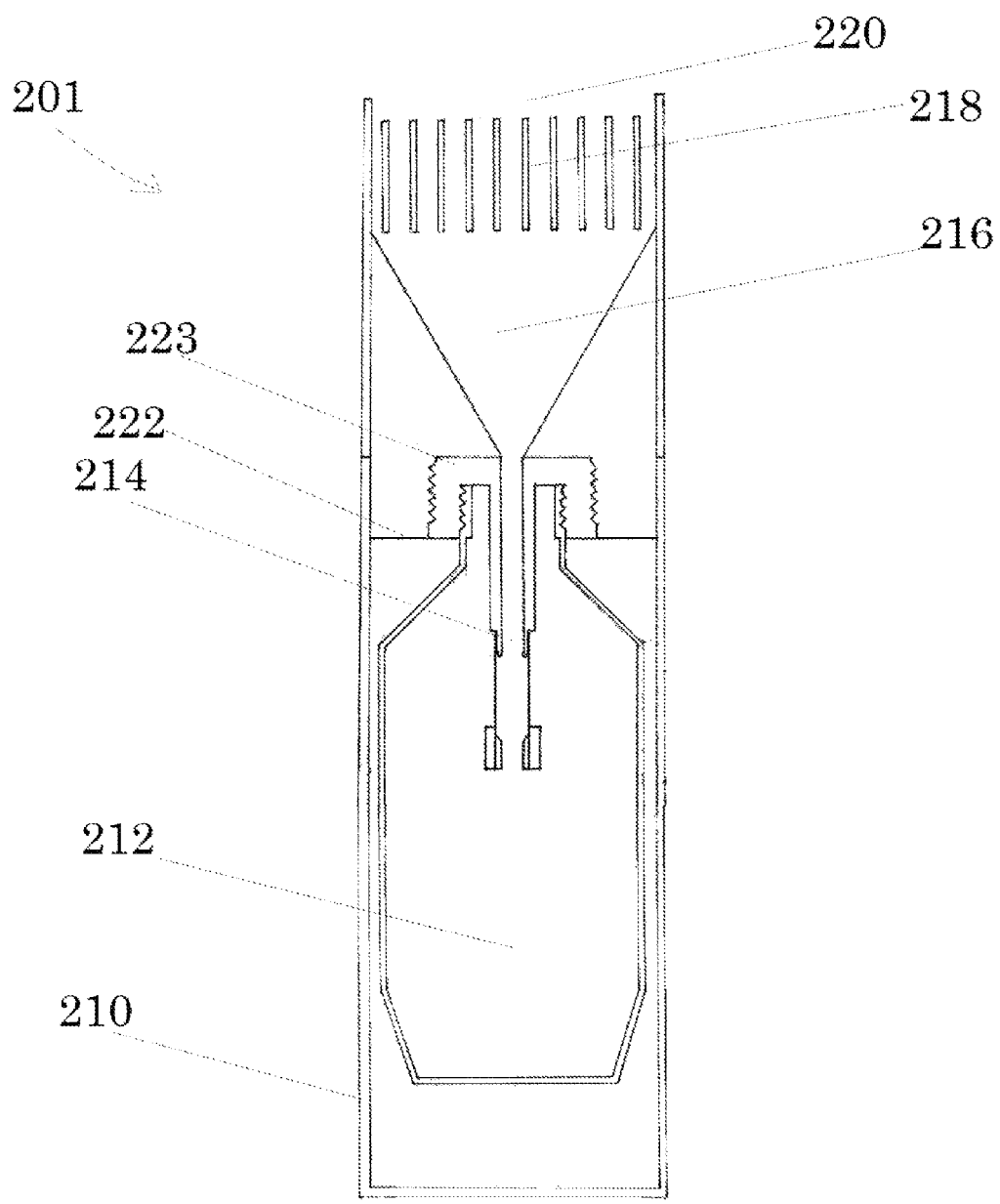
FIG. 5 is a schematic cross-sectional view of a suspended sediment sampler according to a third preferred embodiment of the invention.
Figure 6:
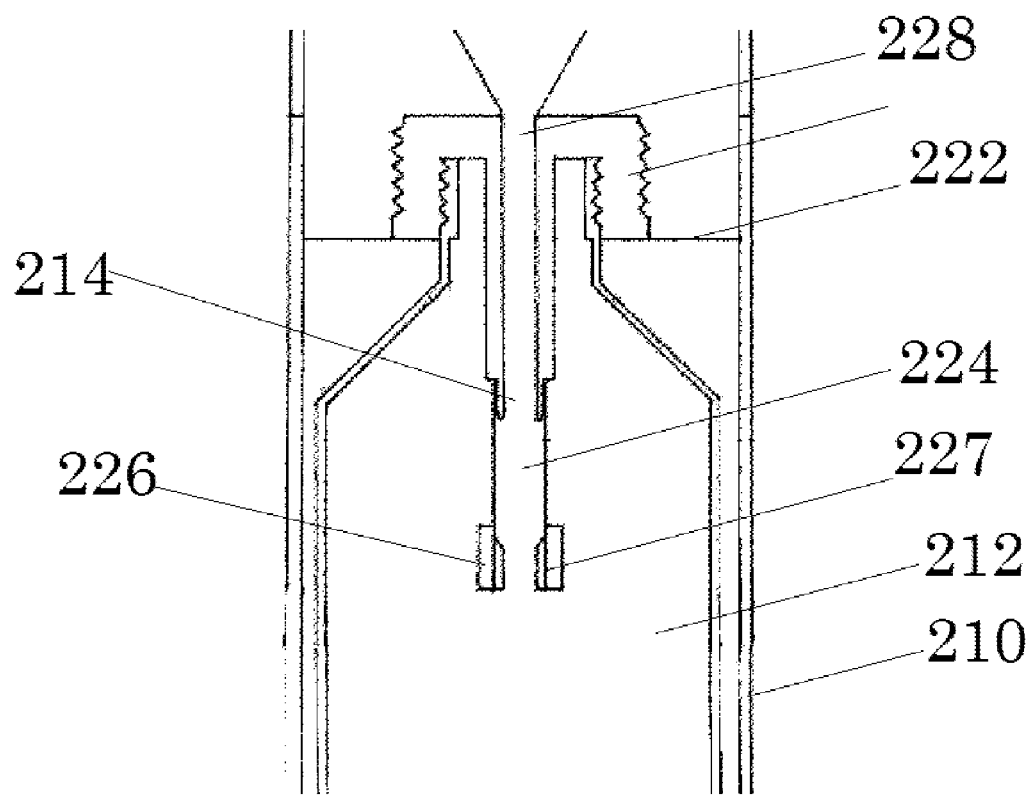
FIG. 6 is a detailed schematic cross-sectional view of the closure mechanism of the sediment sampler of FIG. 5.

Referring to FIGS. 5 and 6, a third preferred embodiment of the invention will be described, similar to the first and second and with similar reference numerals used for ease of reference. Sampler 201 includes housing 210 within which are container 212, closure mechanism 214, funnel 216 and baffles 218, similar to the earlier described embodiments. Sampler 201 and components are made of a rigid plastic but other materials may be used as are suitable to the particular application, for example stainless steel, aluminium or other plastics.

Fluid, such as water, enters through top opening 220 of housing 210, directed by funnel 216 to closure mechanism 214 and into container 212. Container 212 is shown again as a plastic bottle, but other containers may be used instead to collect the sample.

Top opening 220 as illustrated is circular, as housing 210 is cylindrical in shape, circular in cross section and made of plastic, as is funnel 216. Again metal or other materials or combination of metals could be used for housing 210 and funnel 216.

Baffles 218 prevent large materials entering sampler 201 and reduce turbulence improving efficiency. Baffles 218 are made of strips of a plastics material but other suitable materials or combinations of materials could be also be used.

Container 212 is held in place in housing 210 by support 222 attached within housing 210. Neck 223 is attached to support 222 and holds a neck (not labelled) of container 212 in place.

Closure mechanism 214 of the third preferred embodiment works slightly different to those of the first two embodiments. Closure mechanism 214 includes tube 224 and weights 226 and 227, hanging below tube 224. Weights 226 are attached on either side of tube 224. Tube 224 is made of a non-rigid plastic material and weights 226 and 227 under gravity hold tube 226 open in the upright position. Use of non-rigid plastics material for tube 224 means that as sampler 201 tips to one side weights 226 and 227 no longer hang straight down under gravity but also start to tip to one side. As weights 226 and 227 tip tube 224 starts to crumple and block funnel opening 216. As tipping of sampler 201 increases weights 226 and 227 fall further to one side causing tube 224 to fill funnel opening 228. As funnel opening 228 is blocked, when sampler 201 is tipped or inverted loss of the sample is prevented, again assisting to capture a good sample from the sea, for example. Other devices can readily be incorporated within the housing of any of the variant forms of the invention. For example: optical devices; electrochemical devices; electrical devices; mass sensitive devices; magnetic devices; biological devices; flow instruments; pressure instruments; temperature instruments; conductivity instruments; acoustic instruments; chemical measurement instruments; electromagnetic spectrum instruments such as image capturing instruments; communication instruments; mobility instruments; and or global positioning system ("GPS") may be included for additional data collection.

Each of these three forms of closure mechanism 14, 114 and 214 assist samplers 1, 101 and 201 to have significant advantages over existing traps which do not retain the sample inside. For example, the inventive mechanisms are simple to manufacture, use and reuse and yet are extremely efficient at taking a good sediment sample and robust for prolonged or repeated use. The simple nature of the sampler means that it is economic not only to manufacture but also to use, service and maintain, no expensive equipment or specialist training or calibration is required. The size of the sampler can be scaled up or down to suit a particular application and the size of containers 12, 112 and 212 varied accordingly. A particular sampler may be adapted to receive containers of different sizes to suit different applications of the same sampler. The samplers can be readily deployed and retrieved from the surface of a body of water, such as using a boat including a small boat and makes them more readily usable particularly for coastal studies. The easy nature of deployment and retrieval of the sampler improves safety for the users which is of course a highly desirable outcome. Sampler 1, 101 and 201 can also be deployed from above where it is undesirable to contact the fluid, for example, where the fluid to be sampled is a chemical settlement pond.

Overall the inventor has developed a very useful and robust sediment sampler that is easier to use and manufacture than existing samplers with the significant advantage of being able to be inverted and retain the sample inside.

It will be apparent to a person skilled in the art that changes may be made to the embodiments disclosed herein without departing from the spirit and scope of the invention, in its various aspects.

INDUSTRIAL APPLICABILITY

Sediment samplers as described can be manufactured industrially and provided to customers directly or to retailers for on-sale, for use in numerous industries including aquaculture and the resources sector.

| REFERENCE SIGNS LIST: | | |
| --- | --- | --- |
| Embodiment 1 | Embodiment 2 | Embodiment 3 |
| 1 Sampler | 101 Sampler | 201 Sampler |
| 10 Housing | 110 Housing | 210 Housing |
| 12 Container | 112 Container | 212 Container |
| 14 Closure mechanism | 114 Closure mechanism | 214 Closure mechanism |
| 16 Funnel | 116 Funnel | 216 Funnel |
| 18 Baffles | 118 Baffles | 218 Baffles |
| 20 Top opening | 120 Top opening | 220 Top opening |
| 22 Support | 122 Support | 222 Support |
| 23 Neck | 123 Neck | 223 Neck |
| 24 Valve shuttle | 124 Shuttle rod | 224 Tube |
| 26 Recess | 125 Shuttle | 226 Weight |
| 28 Opening of funnel | 126 Rod | 227 Weight |
| | 127 O-ring | 228 Opening of funnel |
| | 128 Opening of funnel | |

The claims defining the invention are as follows:

1. A sampler for sampling sediment suspended in fluid, the sampler including:
   a container including an opening through which fluid can enter and be contained therein; and
   a closure associated with the opening of the container; the closure including a moveable part which on tipping or inversion of the sampler moves between an open and a closed position,
   wherein in the open position the sample can enter the container through the opening and be contained therein, and in the closed position fluid in the container is substantially prevented from leaving the container.

2. The sampler according to claim 1, wherein a housing is included, adapted to correspond to the configuration of the container and the container is held and supported within the housing and a support for the container is included and the support is a planar piece that fits within the housing and is adapted to receive a neck of the container therethrough.

3. The sampler according to claim 1, wherein a funnel is included to direct fluid that enters the sampler into the container and the funnel includes an outlet and the outlet is in fluid communication with the opening of the container to substantially capture fluid that enters the sampler.

4. The sampler according to claim 3, wherein the junction between the funnel and the opening of the container is adapted for receipt of the closure means.

5. The sampler according to of claim 1 wherein the fluid is water containing suspended particulates.

6. The sampler according to claim 1, wherein the closure includes a recess corresponding to a moveable part of the closure, the recess being in communication with the opening, and the moveable part moves into the recess during tipping or inversion to substantially close the opening.

7. The sampler according to claim 1, wherein the closure includes a moveable part with a rounded end and a corresponding recess and during tipping or inversion of the sampler the rounded end of the moveable part falls under gravity into the recess to substantially block the opening and prevent the sample escaping.

8. The sampler according to claim 1, wherein the closure is a shuttle valve including a shuttle and corresponding recess.

9. The sampler according to claim 1, wherein a moveable part is included including a rod moveable between an open position and a closed position, under gravity, to substantially block the opening.

10. The sampler according to claim 9, wherein the rod includes a seal and the seal closes and substantially seals the opening of the container when the sampler is tipped or inverted.

11. The sampler according to claim 8, wherein the rod is a shuttle rod with a shuttle part at one end and a rod at the other and the rod is positioned in the opening such that tipping or inversion of the shuttle rod causes an end of the rod to block the opening.

12. The sampler according to claim 1, wherein the closure includes one or more weight which hangs down under gravity when the sampler is in an upright position and this is the open position in which fluid can pass into the container and further wherein on inversion the weight causes the opening of the container to be substantially closed or blocked preventing fluid from leaving the container.

13. The sampler according to claim 1, wherein the closure includes a tube lying within the opening of the container and fluid entering the sampler can enter the container through the tube in an open position and the sample is substantially prevented from leaving the container in a closed position.

14. The sampler according to claim 13, wherein one or more weight is included suspended below the tube under gravity when the sampler is in the upright position so that the tube allows fluid into the container and as the sampler tips the weight is pulled under gravity closing the tube, to at least some extent.

15. The sampler according to claim 13, wherein the tube deforms or crumples when the sampler is tipped to substantially block the opening and prevent the sample leaving the container.

16. The sampler according to claim 13, wherein the tube must be maintained in a position to allow fluid into the container and in any other position the tube deforms and substantially prevents the sample leaving the container.

17. The sampler according to claim 1, wherein one or more baffles are included to substantially prevent debris entering the sampler and or to reduce turbulence and increase efficiency.

18. The sampler according to claim 1, wherein the sampler includes a device chosen from the following group: optical devices; electrochemical devices; electrical devices; mass sensitive devices; magnetic devices; biological devices; flow instruments; pressure instruments; temperature instruments; conductivity instruments; acoustic instruments; chemical measurement instruments; electromagnetic spectrum instruments such as image capturing instruments; communication instruments; mobility instruments; and or global positioning system ("GPS").

19. A method of use of a sampler for sampling sediment suspended in fluid; the sampler including a container having an opening and a closure associated with the opening including a moveable part, which on tipping or inversion of the sampler, moves between an open and a closed position; the method including the steps of:
   a) deploying the sampler in fluid;
   b) capturing fluid and associated suspended particulates in the sampler over time;
   c) retrieving the sampler;
   and the closure substantially maintains the sample in the container during tipping or inversion of the sampler.

20. The method of claim 19 wherein, the sampler is the sampler of claim 1.

\* \* \* \* \*